(12) United States Patent
Dehnhardt et al.

(10) Patent No.: US 7,582,771 B2
(45) Date of Patent: Sep. 1, 2009

(54) PROCESS FOR THE SYNTHESIS OF CPLA$_2$ INHIBITORS

(75) Inventors: Christoph M. Dehnhardt, New York, NY (US); Sreenivasulu Megati, New York, NY (US); Ronald S. Michalak, Congers, NY (US); Panolil Raveendranath, Monroe, NY (US); Jianxin Ren, Nanuet, NY (US); Charles C. Wu, Denville, NJ (US); Yangzhong Wu, Bronx, NY (US)

(73) Assignee: Wyeth, Madison, NJ (US)

( * ) Notice: Subject to any disclaimer, the term of this patent is extended or adjusted under 35 U.S.C. 154(b) by 617 days.

(21) Appl. No.: 10/930,534

(22) Filed: Aug. 31, 2004

(65) Prior Publication Data

US 2005/0049296 A1    Mar. 3, 2005

Related U.S. Application Data

(60) Provisional application No. 60/499,745, filed on Sep. 3, 2003.

(51) Int. Cl.
*C07D 209/10*    (2006.01)
*C07D 209/14*    (2006.01)
(52) U.S. Cl. .................................. 548/491; 548/503
(58) Field of Classification Search ................ 548/491, 548/503; 514/419
See application file for complete search history.

(56) References Cited

U.S. PATENT DOCUMENTS 6,797,708 B2 * 9/2004 McKew et al. ........... 514/228.2
2005/0148770 A1 * 7/2005 Michalak et al. ............ 544/60

OTHER PUBLICATIONS

Iyer et al., Regiospecific Synthesis of 2-Methoxy-3-methyl-1,4-benzoquinones from Maleoylcobalt Complexes and Alkynes via Lewis Acid Catalysis. A Highly Convergent Route to Isoquinoline Quinones, J. Am. Chem. Soc. 1987, 109, pp. 2759-2770.
Hoffmann et al., Fibrin-Stabilizing Factor Inhibitors. 12.5-Dibenzylaminopentylamine and Related Compounds, a New Type of FSF Inhibitors, Journal of Medicinal Chemistry 1975, vol. 18, No.3, pp. 278-284.
Orazi et al., Synthesis of Fused Heterocycles: 1,2,3,4-Tetrahydroisoquinolines and Ring Homologues via Sulphonamidomethylation, J. chem. Soc. Perkin Trans. I 1986, pp. 1977-1986.
Sonogashira et al., A Convenient Synthesis of Acetylenes : Catalytic Substitutions of Acetylenic Hydrogen with Bromoalkenes, Iodoarenes, and Bromopyridines, Tetrahedron Letters 1975, No. 50, pp. 4467-4470, Pergamon Press, Printed in Great Britain.
Ziegler et al., The Preparation of Alkanesulfonyl Halides, From the Department of Organic Chemistry, Research Division, Sharp and Dohme, Inc., 1951, vol. 16, pp. 621-625.
Taylor et al, Novel 5-Desmethylene Analogues of 5,10-Dideaza-5,6,7,8-tetrahydrofolic Acid as Potential Anticancer Agents, J. Org. Chem. 1992, 57, pp. 3218-3225.
Appleton et al., A Mild and Selective C-3 Reductive Alkylation of Indoles, Tetrahedron Letters 1993, vol. 34, No. 9, pp. 1529-1532, Pergamon Press Ltd, Printed in Great Britain.
Chung et al., A Practical Synthesis of Fibrinogen Receptor Antagonist MK-383. Selective Functionalization of (S)-Tyrosine, Tetrahedron Letters 1993, vol. 49, No. 26, pp. 5767-5776, Pergamon Press Ltd, Printed in Great Britain.
Gandolfi et al., N-Acyl-2-substituted-1,3-thiazolidines, a New Class of Non-narcotic Antitussive Agents: Studies Leading to the Discovery of Ethyl 2-[(2-Methoxyphenoxy)methyl]-β-oxothiazolidine-3-propanoate, J. Med. Chem. 1995, 38, pp. 508-525.
Ezquerra et al., Efficient Reagents for the Synthesis of 5-, 7-, and 5,7-Substituted Indoles Starting from Aromatic Amines: Scope and Limitations, J. Org. Chem. 1996, 61, pp. 5804-5812.
Taylor et al, Novel Methodology for the Preparation of 5-Substituted Tetrahydro[2,3-D]Pyrimidines, Synthetic Communications 1998, 28(1), pp. 1897-1905.
Xiao et al., Regioselective Carbonylative Heteroannulation of o-Iodothiophenols with Allenes and Carbon Monoxide Catalyzed by a Palladium Complex: A Novel and Efficient Access to Thiodhroman-4-one Derivatives, J. Org. Chem. 1999, 64, pp. 9646-9652.

* cited by examiner

*Primary Examiner*—James O. Wilson
*Assistant Examiner*—Ebenezer Sackey
(74) *Attorney, Agent, or Firm*—Fish & Richardson P.C.

(57) ABSTRACT

A process for making the compound of formula (I)

(I)

wherein Ac represents acetate; X represents O or $CH_2$; Y represents $C_1$-$C_6$alkyl; and Z is selected from the group consisting of H, halogen, CN, CHO, $CF_3$, $OCF_3$, OH, $C_1$-$C_6$alkyl, $C_1$-$C_6$alkoxy, $C_1$-$C_6$thioalkyl, $NH_2$, $N(C_1$-$C_6$alkyl)$_2$, $NH(C_1$-$C_6$alkyl), NC(O)—($C_1C_6$alkyl), and $NO_2$. In his process, a compound of formula (II)

(II)

is reacted with hydrazine to form a primary alkylamine, and then the primary alkylamine is reacted with acetic anhydride, to produce the compound of formula (I).

8 Claims, No Drawings

PROCESS FOR THE SYNTHESIS OF CPLA$_2$ INHIBITORS

This application claims priority from copending provisional application(s) No. 60/449,745 filed on Sep. 3, 2003.

FIELD OF THE INVENTION

The present invention relates to a new process for the manufacture of compounds which are inhibitors of the enzyme cytosolic phospholipase A$_2$ (cPLA$_2$).

BACKGROUND OF THE INVENTION

Compounds which inhibit cPLA$_2$ and a process for making those compounds have been disclosed in U.S. patent application Ser. No. 10/302636 filed Nov. 22, 2002, the disclosure of which is incorporated by reference herein. These compounds are useful for a variety of purposes, including the relief of pain and inflammation. In order to bring a drug to market, it is necessary to have an economically feasible process for making the compound. Often, a process that works in the laboratory is not practical from a commercial standpoint. It would be desirable to have a relatively inexpensive and efficient method for making at least some of the aforesaid compounds.

A method for preparing tetrahydropyrido[2,3-d]pyrimidines functionalized at the 5-posiiton starting from acyclic aldehydes is taught by Watson in *Synthetic Communications*, 28(10), 1897-1905 (1998).

Appleton, et al., in *Tetrahedron Lett*. 1993, 34, 1529, teach reductive C-3 alkylation of 3-unsubstituted indoles to produce C-3 functionalized indoles, especially 3-(arylmethyl) indoles and 3-(heteroarylmethyl)indoles. In the reference reaction, the initial indole is reacted with an aldehyde or ketone using triethylsilane and trifluoroacetic acid.

A process that includes the coupling of a 2-amino-4,6-dichloropyrimidine with but-3-ynylamine to form an N-pyrimidinyl-but-3-ynylamine, which is then coupled with a 4-substituted iodophenyl compound is disclosed by Taylor, et al., in *J. Org. Chem.*, 57, 3218-3225 (1992). The reaction of the pyrimidylbutynylamine and the iodophenyl compound preserves the triple bond and is carried out in the presence of PdCl$_2$, PPh$_3$ and CuI. In the reference process, hydrogenation of the triple bond is carried out subsequently.

A method for synthesizing N-but-3-ynylphthalimide is taught by Hoffmann, et al., *J. Med. Chem.*, 18(3), 278-284 (1975). In this method, phthalic acid anhydride is reacted with 4-amino-1-butyne in glacial acetic acid to produce the target compound. Iyer et al., *J. Am. Chem. Soc.*, 109, 2759-2770(1987), provide a synthetic method using a Mitsunobo reaction.

Ezquerra, et al., *J. Org. Chem.*, 61(17), 5804-5812 (1996), have described the formation of an indole by iodinating a substituted aniline followed by reaction with (trimethylsilyl) ethyne in the presence of Pd(PPh$_3$)$_2$Cl$_2$, CuI and triethylamine to form a [(trimethylsilyl)ethynyl]aniline. This reaction follows the general theme for synthesizing arylacetylenes taught earlier by Sonogashira, et al., *Tetrahedron Letters*, 50, 4467-4470 (1975).

Xiao, et al., *J. Org. Chem.*, 64, 9646-9652 (1999), have described a preparation for 2-iodoaniline in which a 4-substituted aniline is reacted with iodine in an aqueous sodium bicarbonate solution. The authors also describe using 2-iodoaniline in the synthesis of other compounds.

SUMMARY OF THE INVENTION

The present invention comprises a process for making the compound of formula (I)

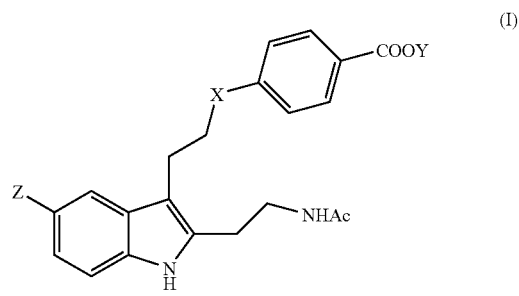

wherein Ac represents acetate; X represents O or CH$_2$; Y represents C$_1$-C$_6$alkyl; and Z is selected from the group consisting of H, halogen, CN, CHO, CF$_3$, OCF$_3$, OH, C$_1$-C$_6$alkyl, C$_1$-C$_6$alkoxy, C$_1$-C$_6$thioalkyl, NH$_2$, N(C$_1$-C$_6$alkyl)$_2$, NH(C$_1$-C$_6$alkyl), NC(O)-(C$_1$-C$_6$alkyl), and NO$_2$, said process comprising reacting the compound of formula (II)

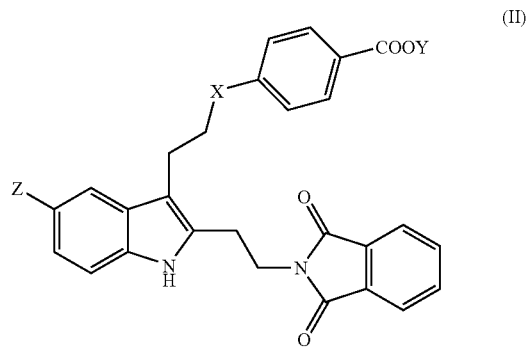

with hydrazine to produce the intermediate compound

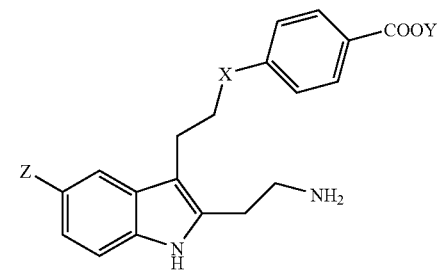

and then reacting the intermediate compound with acetic anhydride to form the compound of formula (I).

The compound of formula (I) may be used to make compounds which act to inhibit cPLA$_2$. The process of this invention provides a novel and efficient route to make compounds of formula (I), and cPLA$_2$ inhibitors which may be obtained by using such compounds.

The invention further comprises compounds produced by the process of the invention.

Various objects and advantages of the present invention will be apparent to those skilled in the art from the description below and the appended claims.

DETAILED DESCRIPTION OF THE PREFERRED EMBODIMENTS

The present invention provides a new method for making compounds of formula (I), shown above, which are useful for making cPLA$_2$ inhibitors. In preferred embodiments of the present invention, Z is halogen (F, Cl, Br, or I), most preferably Cl, Y is methyl or ethyl, and/or X is CH$_2$.

In a preferred embodiment of this method, in the reaction of a compound of formula (II) with hydrazine, hydrazine hydrate in a suitable solvent is used. Those skilled in the art will be able to determine which solvents are suitable without undue experimentation; a few examples of suitable solvents include acetonitrile, methanol, ethanol, propanol, and the like. The subsequent reaction with acetic anhydride preferably takes place in a polar aprotic solvent, especially in pyridine, or the like.

Compounds of formula (II) may be made by reacting a compound of the formula (V)

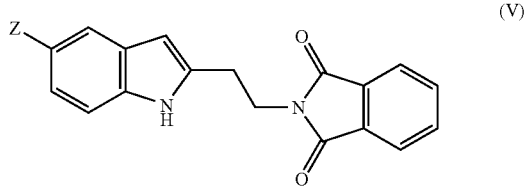

with a compound of the formula (VI)

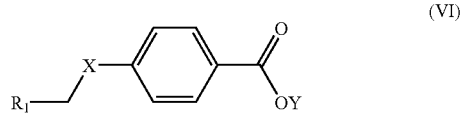

wherein R$_1$ represents CHO or CH(OY)$_2$ and each Y is independently selected from alkyl groups of 1 to 6 carbon atoms. Preferably, this reaction is performed in a solution containing the reactants and triethylsilane, in a suitable solvent such as dichloromethane, or the like, and trifluoroacetic acid is added slowly over a period of about 15-60 min or more until the reaction is complete.

In a preferred embodiment of this invention, the compound of formula (V) is obtained by the following reaction steps:

a)

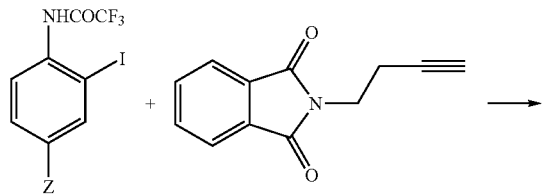

-continued

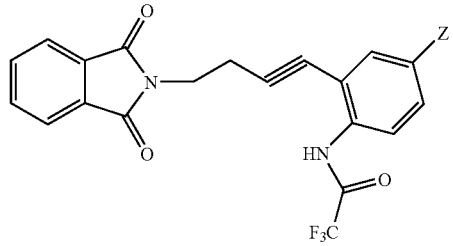

preferably in the presence of a dilute solution of CuI, triethylamine and PdCl$_2$bis(triphenyphosphine) in a solvent such as THF; and then, b) heating the product compound to form the compound of formula (V). In a highly preferred embodiment, step b) is carried out in piperidine and N,N-dimethylformamide at a temperature of approximately 100° C. The reactants in this step a) are known compounds, and can readily be obtained by those skilled in the art.

For example, in one method for obtaining preferred compounds in this invention, the process begins with the ortho-iodination of 4-haloaniline using iodine in aqueous sodium bicarbonate to give the known 4-halo-2-iodoaniline. This product, optionally isolated, is converted to the N-trifluoroacetamide using trifluoroacetic anhydride and triethylamine in a suitable inert solvent (toluene, THF, MeCN). Protection of the nitrogen as a trifluoroacetamide is beneficial in the cyclization step b), where an unprotected nitrogen atom gives much lower yields and difficult product isolation and purification. The trifluoroacetamide is coupled with the known phthalimidobutyne to provide an intermediate arylacetylene that can be optionally isolated, but can also be carried forward without isolation into the cyclization step to provide the indole compound (V). These coupling and cyclization reactions are known as Sonogashira and Castro reactions and are mediated by catalytic palladium and copper salts.

In a further preferred embodiment of the present invention, compound (V) is alkylated with a known aldehyde or acetal using the reagent combination triethylsilane and trifluoroacetic acid (TFA) in a suitable inert solvent to produce a compound of formula (II). This type of reductive C-3 alkylation reaction of indoles is known in the art, for example, see Appleton, et al., *Tetrahedron Lett.* 1993, 34, 1529. The phthaloyl protecting group then may be selectively removed from (II) using hydrazine hydrate in a suitable solvent (acetonitrile, low MW alcohols) to form an intermediate amine compound.

After the compound of formula (II) is converted to the intermediate compound as described above, the latter compound may be isolated, but preferentially is carried forward without isolation into an N-acetylation step in which the intermediate compound is reacted with an acetylating agent such as Ac$_2$O or acetyl chloride in a suitable inert solvent to form a compound of formula (I). If the solvent is water-soluble the N-acetyl product will be easily isolated by precipitation caused by water addition to the reaction mixture.

The resulting N-acetyl compound of formula (I) preferably is combined with potassium t-butoxide, benzhydryl bromide, and acetonitrile to make an N-benzhydrylated compound of formula (III)

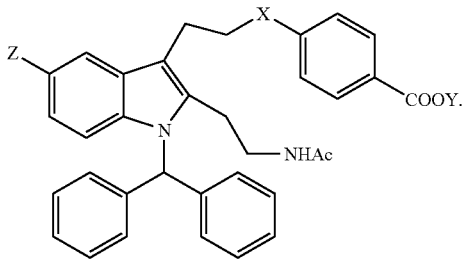

(III)

The ester group of the N-benzhydrylated compound (III) may be selectively hydrolyzed, preferably by using a mixture of aqueous potassium or sodium hydroxide and inert organic solvents to afford the corresponding carboxylic acid, which can be purified by using a slurry in warm EtOAc, $CH_3CN$ or low molecular weight alcohol (such as methanol, ethanol, propanol, and the like). The partial hydrolyses of the ester to a carboxylic acid is beneficial because these intermediates have favorable physical properties that allow facile purification, and without this ester hydrolysis, the intermediates most likely must be purified by chromatography before a one-step cleavage of ester and amide groups is performed.

The N-acetyl amide bond of the carboxylic acid then may be cleaved using a mixture of aqueous potassium hydroxide, methanol and water, known in the art as Claisen alkali conditions, to produce an amino acid. This amino acid may be reacted with a compound R-A-$(CH_2)_n$—$S(O)_2Cl$ to form a compound of formula (IV)

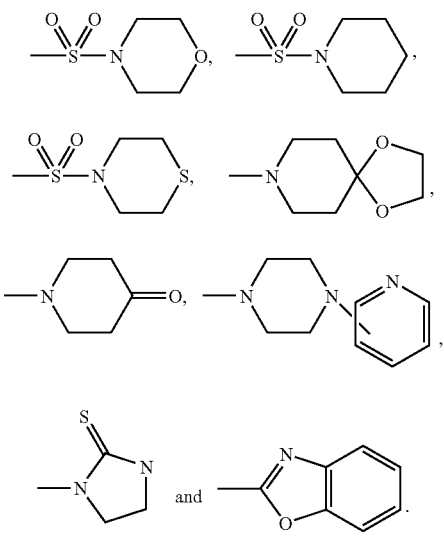

(IV)

wherein n represents an integer from 0 to 4;
A is a chemical bond, —S—, —O—, —S(O)—, —S(O)$_2$—, —NH—, —NHC(O)—, —C≡C—,

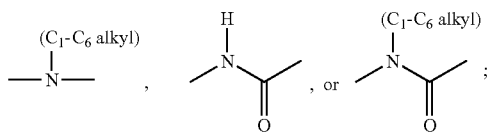

and R is a moiety selected from the group consisting of $C_1$-$C_6$ alkyl, $C_1$-$C_6$ fluorinated alkyl, $C_3$-$C_6$ cycloalkyl, tetrahydropyranyl, camphoryl, adamantyl, CN, —N($C_1$-$C_6$ alkyl)$_2$, phenyl, pyridinyl, pyrimidinyl, furyl, thienyl, napthyl, morpholinyl, triazolyl, pyrazolyl, piperidinyl, pyrrolidinyl, imidazolyl, piperizinyl, thiazolidinyl, thiomorpholinyl, tetrazole, indole, benzoxazole, benzofuran, imidazolidine-2-thione, 7,7,dimethyl-bicyclo[2.2.1]heptan-2-one, benzo[1,2,5]oxadiazole, 2-oxa-5-aza-bicyclo[2.2.1]heptane, piperazin-2-one or pyrrolyl groups, each optionally substituted by from 1 to 3 substituents independently selected from H, halogen, —CN, —CHO, —$CF_3$, $OCF_3$, —OH, —$C_1$-$C_6$ alkyl, $C_1$-$C_6$ alkoxy, —$NH_2$, —N($C_1$-$C_6$)$_2$, —NH($C_1$-$C_6$), —N—C(O)—($C_1$-$C_6$), —$NO_2$, —$SO_2$($C_1$-$C_3$ alkyl), —$SO_2NH_2$, —$SO_2NH(C_1$-$C_3$ alkyl), —$SO_2N(C_1$-$C_3$ alkyl)$_2$, —COOH, —$CH_2$—COOH, —$CH_2$—N($C_1$-$C_6$ alkyl), —$CH_2$—N($C_1$-$C_6$ alkyl)$_2$, —$CH_2$—$NH_2$, pyridine, 2-methyl-thiazole, morpholino, 1-chloro-2-methyl-propyl, —$C_1$-$C_6$thioalkyl, phenyl optionally substituted with one or more halogen atoms, benzyloxy, ($C_1$-$C_3$ alkyl)C(O)$CH_3$, ($C_1$-$C_3$ alkyl)O$CH_3$, C(O)$NH_2$, Preferably, n=1, A is a chemical bond, and R represents phenyl optionally substituted with from one to three halogen atoms.

The compound of formula (IV) may be converted to a pharmaceutically acceptable salt or ester thereof.

In one preferred embodiment of this process, the amino acid is reacted with bistrimethylsilyltrifluoroacetamide, which converts the carboxylic acid group to a trimethylsilyl ester. Addition of a base such as pyridine and (3,4-dichlorophenyl)-methanesulfonyl chloride results in formation of an intermediate sulfonamide. The in situ trimethylsilyl protecting groups are cleaved during the aqueous extractive workup to provide a compound of formula (IV) in which $(CH_2)_n$-A-R is a 3,4-dichlorophenylmethyl group. Impurities formed during the N-benzhydrylation step may be removed at this point, preferentially by one recrystallization from toluene or toluene and heptane mixtures, or from EtOAc and heptane mixtures, or the like.

A highly preferred embodiment of the process steps described above is illustrated in the following scheme:

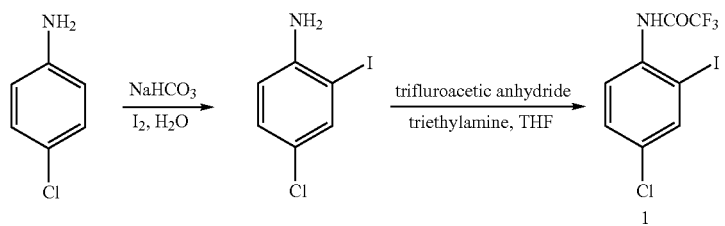
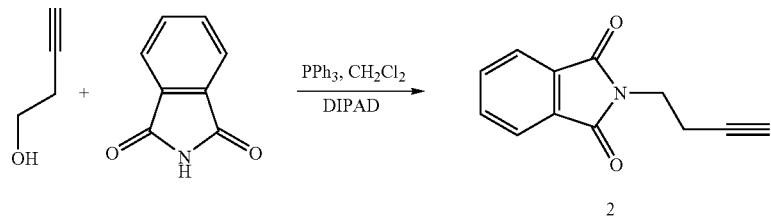
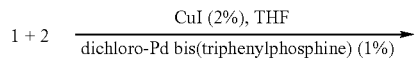
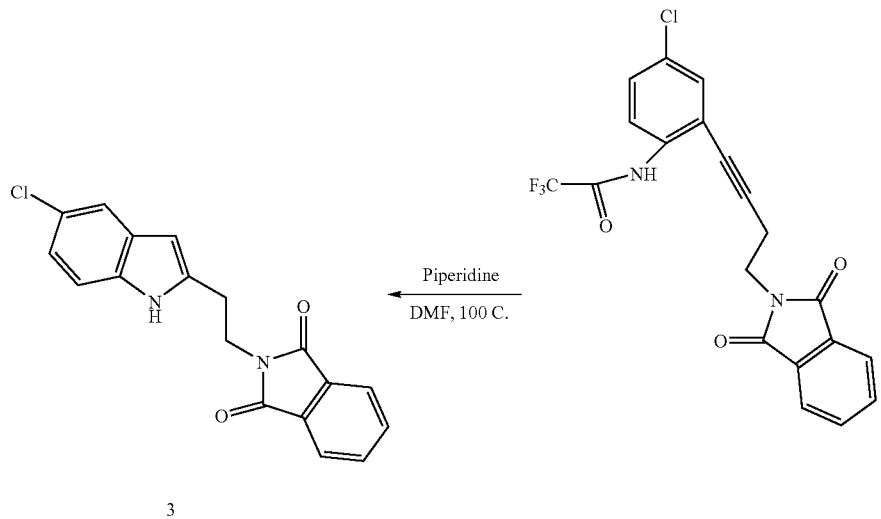
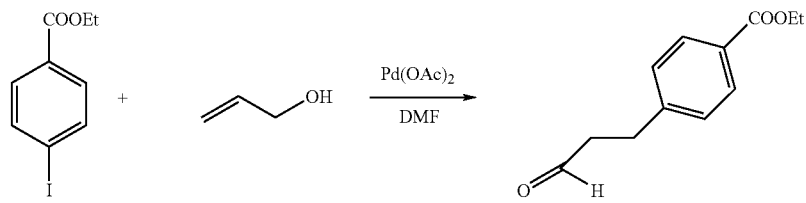
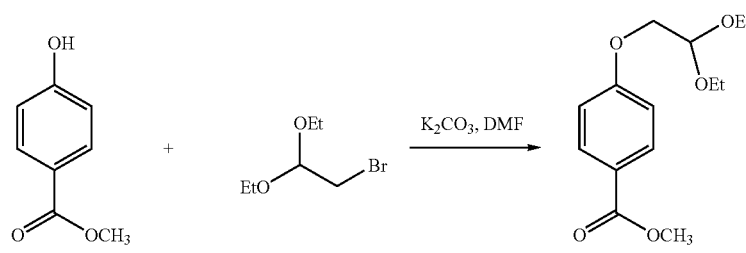

-continued
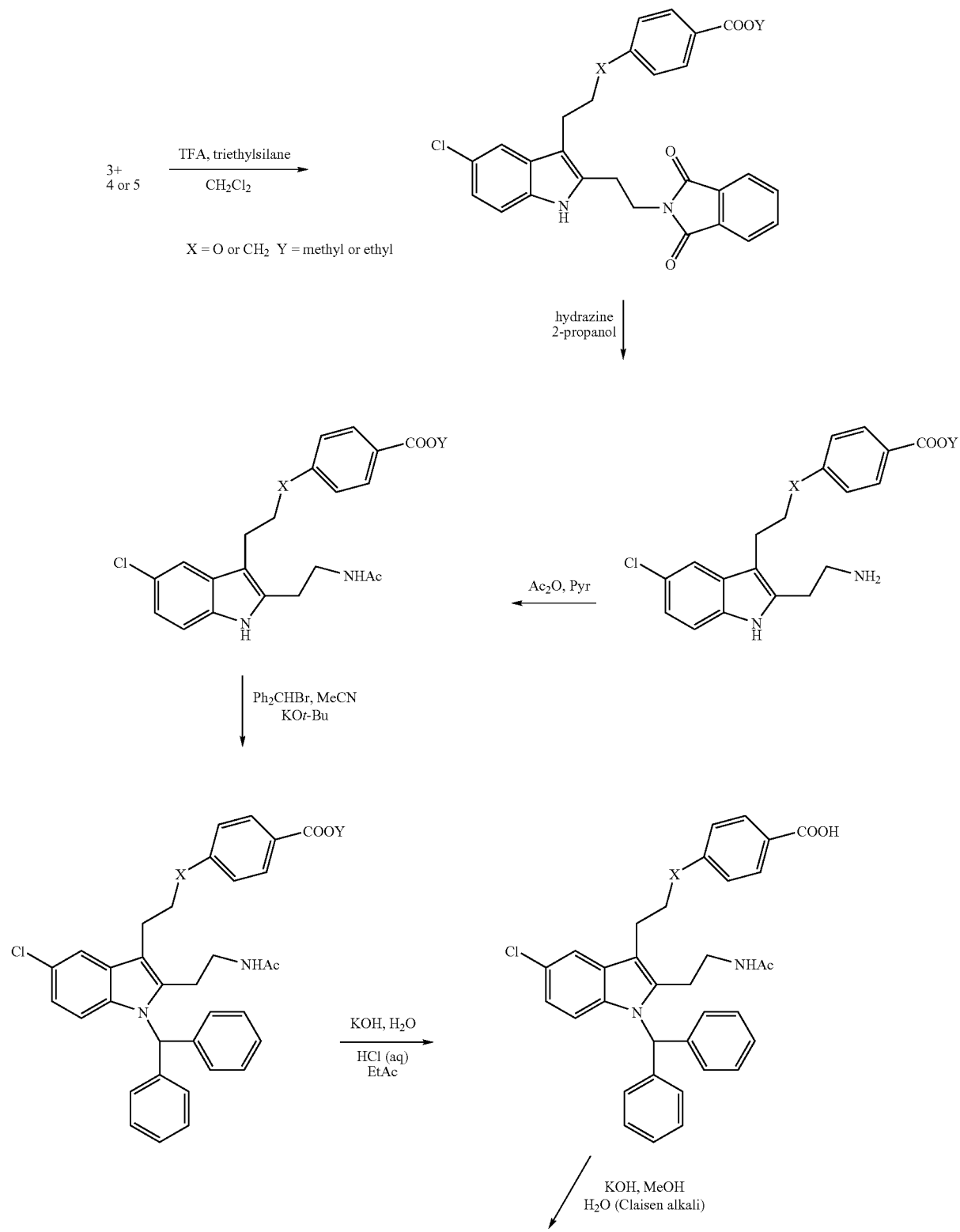

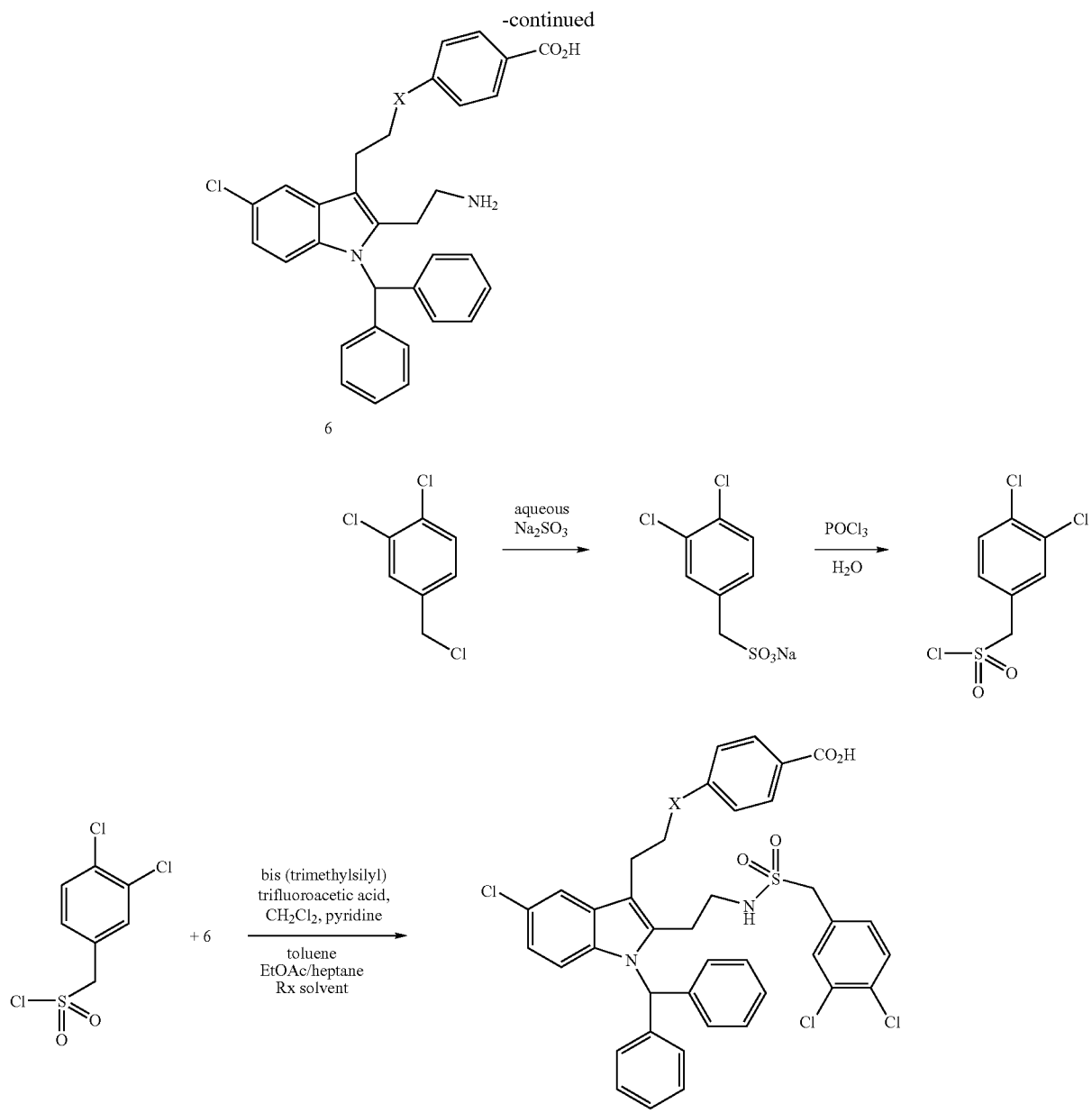

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains an acidic moiety.

Pharmaceutically acceptable esters can be formed from reaction with an alcohol, for example a $C_1$-$C_6$ alkanol, when a compound of this invention contains an acidic moiety.

The following examples are presented to illustrate certain embodiments of the present invention, but should not be construed as limiting the scope of this invention.

EXAMPLE 1

Preparation of
N-(4-Chloro-2-iodophenyl)-2,2,2-trifluoroacetamide

Trifluoroacetic anhydride (2.02 kg, 9.64 mol) is added to a cold (0-5° C.), stirred solution of 4-chloro-2-iodoaniline (2.37 kg, 8.76 mol), triethylamine (1.11 kg, 11.0 mol), and toluene (7.8 L) at a rate that maintains the reaction temperature below 20° C. The reaction mixture is stirred for 30 min. Methanol (100 mL) is added to the reaction mixture to consume excess trifluoroacetic anhydride. The mixture is washed with water (5.5 L) and concentrated under reduced pressure to a volume of 5-6 L. The mixture is diluted with ethanol (4 L) and concentrated under reduced pressure to a volume of 5-6 L. The mixture is diluted with ethanol (4 L). Water (10 L) is added to the stirred mixture over 1 hour. The mixture is cooled (0-5° C.) and the solid is collected by filtration and dried to give N-(4-Chloro-2-iodophenyl)-2,2,2-trifluoroacetamide (2.78 kg, 82%, 99.25% purity, largest single impurity 0.75%). $^1$H NMR (CDCl$_3$): δ8.25 (br s, 1H), 8.15 (d, 1H, J=8.7 Hz), 7.83 (d, 1H, J=2.3 Hz, 7.40 (dd, 1H, J=2.3 Hz, 8.7 Hz).

EXAMPLE 2

Preparation of 2-[2-(5-Chloro-1H-indol-2-yl)-ethyl]-isoindole-1,3-dione

Dichlorobis(triphenylphosphine)palladium (II) (43 g, 0.061 mol), copper (I) iodide (20.2 g, 0.106 mol), and triethylamine (782 g, 7.74 mol) is added to a stirred mixture of N-(4-Chloro-2-iodophenyl)-2,2,2-trifluoroacetamide (1800 g, 5.15 mol) and tetrahydrofuran (1.80 L). A solution of 2-(but-3-ynyl)-1H-isoindole-1,3(2H)-dione (1098 g, 5.51 mol) and tetrahydrofuran (11 L) is added to the reaction mixture slowly over 6 hours, maintaining a reaction temperature of 30° C. The reaction mixture is allowed to stir at room temperature overnight. The reaction mixture is filtered under reduced pressure and the triethylammonium iodide cake is washed with tetrahydrofuran (2×550 mL). The filtrate is concentrated under reduced pressure to a volume of less than 6 L, and N,N-dimethylformamide (8 L) is added to the residue. The mixture is concentrated until tetrahydrofuran is removed. Piperidine (535 g, 6.29 mol) is added to the mixture. The mixture is stirred and warmed to 100° C. The mixture is maintained at 100° C. until the product/starting material ratio is >97/3. The mixture is cooled to 32° C. Water (4.2 L) is added to the stirred mixture over >100 min, allowing the temperature of the mixture to rise to 45° C. The mixture is cooled (0-5° C.). The product is collected by filtration and dried to give 2-[2-(5-Chloro-1H-indol-2-yl)-ethyl]-isoindole-1,3-dione (1173 g, 73%, 98.1% purity, largest single impurity 1.2%). $^1$H NMR (DMSO-$_{d6}$): δ11.35 (s, 1H), 7.83 (m, 4H), 7.41 (d, 1H, J=2.0 Hz), 7.29 (d, 1H, J=8.6 Hz), 6.99 (dd, 1H, J=2.0, 8.6 Hz), 3.94 (t, 2H, J=7.1 Hz), 3.08 (t, 2H, J=7.1 Hz).

EXAMPLE 3

4-(3-Oxo-propyl)-benzoic Acid Ethyl Ester

Ethyl 4-iodobenzoate (200 g, 0.725 mol) and allyl alcohol (63 g, 1.087 mol) are added to a stirred suspension of Sodium bicarbonate (152 g, 1.812 mol), tetrabutyl-ammounium bromide (117 g, 0.362 mol) and Palladium (II) acetate (3.2 g, 0.014 mol) in DMF (600 mL). The reaction mixture is warmed to 75-80° C. for 3-3.5 hours and cooled to 40° C.-50° C. Toluene (1 L) is added to the reaction mixture with vigorous agitation and the mixture is stirred for 15 min at room temperature. The resulting mixture is filtered through a celite pad. The pad is washed with toluene (2×200 mL). The filtrate and wash are combined, washed with water (3×1 L), evaporated to constant weight at 30° C.-40° C. and 10 mmHg. The crude product 147.5 g (98.8%, 84% by HPLC) of 4-(3-Oxo-propyl)-benzoic acid ethyl ester as dark brown oil is obtained and can be used in the next step without further purification.

$^1$H NMR (DMSO-d$_6$): δ1.38(t, 3H), 2.81(t, 2H), 3.03(t, 2H), 4.39(q, 2H), 7.27(d, 2H), 7.98(d, 2H), 9.81 (s, 1H).

EXAMPLE 4

Preparation of 4-(2-{5-Chloro-2-[2-(1,3-dioxo-1,3-dihydro-isoindol-2-yl)-ethyl]-1H-indol-3-yl}-ethoxy)-benzoic Acid Methyl Ester To a solution 4-(2,2-diethoxy-ethoxy)-benzoic acid methyl ester (495 g, 1.84 mol), triethylsilane ((536 g, 4.62 mol) and 2-[2-(5-chloro-1 H-indol-2-yl]-ethyl]-isoindole-1,3-dione (500 g, 1.54 mol) in dichloromethane (3.5 L) was added trifloroacetic acid (878 g, 7.7 mol) during a period of 1 hour. Then, the reaction mixture was cooled to 0-10° C. A mixture of triethyl amine (787 g) and methanol (4 L) was added during a period of 45 min. The reaction mixture was stirred for 1 h at 0-10° C. and filtered. The crude product was washed with methanol (2×1000 mL) and dried to give a white solid (483 g) in 62% yields and 88.1% area purity. $^1$H NMR (CDCl$_3$): δ6.9-8.6 (m, Ph, CHPh$_2$), 4.13 (t, 2H, J=6.6 Hz), 4.04 (t, 2H, J=7.2 Hz), 4.13 (t, 2H, J=6.6 Hz), 3.87 (S, 3H), 3.23 (t, 2H, J=7.2 Hz), 3.16 (t, 2H, J=6.6 Hz).

EXAMPLE 5

Synthesis of 4-(3-{5-Chloro-2-[2-(1,3-dioxo-1,3-dihydro-isoindol-2-yl)-ethyl]-1H-indol-3-yl}-propyl)-benzoic Acid Ethyl Ester To a solution 4-(3-oxo-propyl)-)-benzoic acid ethyl ester (381 g, 1.85 mol), triethylsilane ((537 g, 4.62 mol) and 2-[2-(5-chloro-1 H-indol-2-yl]-ethyl]-isoindole-1,3-dione (500 g, 1.54 mol) in dichloromethane (4 L) was added trifloroacetic acid (878 g, 7.7 mol) during a period of 1 hour. Then, the reaction mixture was cooled to 0-10° C. A mixture of triethyl amine (778 g) and methanol (3 L) was added during a period of 45 min. The reaction mixture was stirred for 1 h at 0-10° C. and filtered. The crude product was washed with methanol (2×1000 mL) and dried to give a white solid (313 g) in 50% yield. $^1$H NMR (CDCl$_3$): δ6.9-8.2 (m, Ph, CHPh$_2$), 4.35 (dd, 2H, J=14.3 Hz, 7.2 Hz), 3.99 (t, 2H, J=7.1 Hz), 3.13 (t, 2H, J=7.2 Hz), 2.69 (t, 4H, J=7.3 Hz) 1.90 (m, 2H), 1.38 (t, 3H, J=7.1 Hz).

EXAMPLE 6

Synthesis of 4-{2-[2-(2-Acetylamino-ethyl)-5-chloro-1H-indol-3-yl]-ethoxy}-benzoic Acid Methyl Ester Hydrazine hydrate (174 g, 3 mol) was added in one portion to a stirred suspension of 4-(2-{5-Chloro-2-[2-(1,3-dioxo-1,3-dihydro-isoindol-2-yl)-ethyl]-1H-indol-3-yl}-ethoxy)-benzoic acid methyl ester (503 g, 1.0 mol) in 5.7 L 2-propanol. The suspension was warmed to 82 C for 3.5 h. HPLC analysis showed remaining starting material was less than 1%. The reaction mixture was allowed to cool to 70° C. and filtered at this temperature. Pyridine (1 L) was added to the filtrate, and the 2-propanol was distilled in vacuo (40C, 50 mmHg). The concentrate was charged to a 12 L 4-neck flask equipped with mechanical stirrer. The mixture was cooled to 5° C. under stirring. Acetic anhydride (113 g, 1.1 mol) was added dropwise maintaining an internal temperature below 10 C. The mixture was stirred for 0.5 h after complete acetic anhydride addition. HPLC analysis showed less 1% of amine remaining. Water (5 L) was added and the resulting suspension was stirred for 12 h at rt. The solid was collected by filtration and washed with water (3×500 mL). The product was dried in a vacuum oven at 50C to an LOD of <1%. 1H-NMR (300 MHz, DMSO$_{d6}$): δ1.78 (s, 3H), 2.87 (t, J=7 Hz, 2H), 3.10 (t, J=7 Hz, 2H), 3.36 (t, J=7 Hz, 2H), 3.80 (s, 3H), 4.16 (t, J=7 Hz, 2H), 6.98-7.03 (m, 3H), 7.26 (d, J=9 Hz, 1H), 7.57 (d, J=2 Hz, 1H), 7.88 (d, J=9 Hz, 2H), 8.00 (t, J=6 Hz, 1H), 10.90 (s, 1H) ppm

EXAMPLE 7

4-{3-[2-(2-Acetylamino-ethyl)-5-chloro-1H-indol-3-yl]-propyl}-benzoic Acid Ethyl Ester A stirred mixture of 4-(3-{5-chloro-2-[2-(1,3-dioxo-1,3-dihydro-isoindol-2-yl)-ethyl]-1H-indol-3-yl}-propyl)-benzoic acid ethyl ester (415 g, 0.81 mol) and 55% hydrazine solution (141 g, 2.42 mol) in 2-propanol (4 L) is warmed to 80° C. for 3 h-4 h. The reaction is complete when the product/starting material ratio is greater than 99/1 by HPLC. The reaction mixture is cooled to room temperature. The byproduct is removed by filtration. The cake is washed with 2-propanol (400 mL×3). The filtrate and wash are combined and distilled to about half volume. Pyridine (830 mL×2) is added and the remainder of the 2-propanol is removed under reduced pressure. The stirred mixture is cooled to 5° C.-10° C. Acetic anhydride (90.4 g, 1.10 mol) is added dropwise to the reaction mixture at 5° C.-10° C. The reaction is complete when the product/starting material ratio is >99/1 by HPLC analysis. Water (5.0 L) is added to the reaction mixture, maintaining the temperature below 25° C. The reaction mixture is stirred at room temperature for 12 hours. The solid product is collected by filtration, washed with water (500 mL×3) and dried in vacuum oven (70° C.) to give 303 g (87.6%, 95.4% by HPLC) of 4-{3-[2-(2-Acetylamino-ethyl)-5-chloro-1H-indol-3-yl]-propyl}-benzoic acid ethyl ester.

$^1$H NMR (DMSO-d$_6$) δ1.30(t, 3H), 1.77(s, 3H), 1.86(br.m, 2H), 2.73(br.m, 4H), 2.82(br.m, 2H), 3.30(br.m, 2H), 4.28(q, 2H), 6.99(dd, 1H), 7.25(d, 1H), 7.36(s, 1H), 7.38(dd, 2H), 7.84(d, 2H), 7.97(br.t, 1H), 11.00(br.s, 1H).

EXAMPLE 8

Synthesis of 4-{2-[2-(2-Acetylamino-ethyl)-1-benzhydryl-5-chloro-1H-indol-3-yl]-ethoxy-benzoic Acid Methyl Ester Bromodiphenylmethane (208.3 g 0.843 mol) and 4-{2-[2-(2-Acetylamino-ethyl)-5-chloro-1H-indol-3-yl]-ethoxy-benzoic acid methyl ester (250.0 g, 0.603 mol) were suspended in acetonitrile (10 L). The suspension was stirred and cooled to −1 C and potassium tert. butoxide (94.6 g 0.843 mol) was added in one portion. the reaction was complete by HPLC analysis after stirring for 2.5 h at −1 C. Water (125 mL) was added to the reaction mixture. The suspension was heated to 50 C and then 8.3 L solvent was removed by vacuum distillation (180 mmHg). Aqueous Potassium hydroxide (84.4 g KOH (87%) in 300 mL of water) was added and the reaction mixture was refluxed for 3 h. The solution was cooled to 35 C and acidified (pH=3) with 4N hydrochloric acid (435 mL). The suspension was stirred for 20 min. at 5 C and the precipitate was collected by filtration. The cake was washed with water (250 mL×3) and ethyl acetate (250 mL) and the wet cake was dried at 70 C/30 mmHg for 36 h to yield 253 g crude product. The solid was suspended with 1 L ethylacetate and stirred and warmed at refluxed for 4 h. This ethylacetate slurry was repeated two times. The wet product was collected by filtration and dried for 16 h at 60 C/30 mmHg to obtain 177.3 g (50%) product. The structure was determined by $^1$H-NMR. δ(300 MHz, DMSO$_{d6}$) 1.78 (s, 3H), 2.97 (m, 2H), 3.15-3.25 (m, 4H), 4.22 (t, J=6 Hz, 2H), 6.48 (d, J=9 Hz, 1H), 6.80 (dd, J=2 Hz, J=9 Hz, 1H), 6.87 (d, J=8 Hz, 2H), 7.10-7.13 (m, 4H), 7.26 (s, 1H), 7.31-7.40 (m, 6H), 7.66 (d, J=2 Hz, 1H), 7.85 (d, J=8 Hz, 2H), 8.15 (t, J=5 Hz, 1H) ppm.

EXAMPLE 9

4-{3-[2-(2-Acetylamino-ethyl)-1-benzhydryl-5-chloro-1H-indol-3-yl]-propyl}-benzoic Acid To a suspension of the 4-{3-[2-(2-Acetylamino-ethyl)-5-chloro-1H-indol-3-yl]-propyl}-benzoic acid ethyl ester (250.0 g, 0.585 mol, WAY-185133) and bromodiphenylmethane (203.0 g, 0.82 mol) in acetonitrile (10.0 L) at 3° C. was added potasssium tert.butoxide (92.0 g, 0.82 mol). The reaction mixture was stirred for 7 hours at 3° C. Water (125 ml) was added to the reaction mixture and then 7.5 L of solvent was distilled off. To the concentrated reaction mixture, potassium hydroxide (82.1 g, 1.46 mol) was added followed by 2 hours of reflux. To the cooled reaction mixture at 35° C., dil. HCl was added to bring pH to 4-5. The reaction mixture suspension was then cooled to 3° C. It was then filtered, washed with water (250 mL×2). The wet cake was slurried in ethyl acetate (750 ml) at reflux for 2 h. The suspension was cooled to ambient temperature, filtered and washed with ethyl acetate (85 mL×2). Drying the product in vacuo at 50° C. provided 177.5 g (yield 54%, HPLC 93%, SLI 1.4%) of 4-{3-[2-(2-Acetylamino-ethyl)-1-benzhydryl-5-chloro-1H-indol-3-yl]-propyl}-benzoic acid (WAY-185008). Mass spectrum (electrospray, m/e): M+H 565. $^1$H NMR (DMSO$_{-d6}$): δ12.30 (br.s, 1H), 8.06 (m,1H), 7.86 (m, 2H), 7.45 (d, 1H, J=3 Hz), 7.34 (m, 6H), 7.21 (s, 1H), 7.12 (m, 4H), 6.77 (dd, 1H, J=9 Hz& 3 Hz), 6.45 (d,1H, J=9 Hz), 3.28 (m, 2H), 2.87 (m, 2H), 2.72 (m, 4H), 1.90 (m, 2H).

EXAMPLE 10

4-{2-[2-(2-Amino-ethyl)-1-benzhydryl-5-chloro-1H-indol-3-yl]-ethoxy}-benzoic Acid Methanol (660 mL), water (165 mL) and potassium hydroxide (365 g, 5.53 mol) was combined with 4-{2-[2-(2-Acetylamino-ethyl)-1-benzhydryl-5-chloro-1H-indol-3-yl]-ethoxy}-benzoic acid (165 g, 0.291 mol). The reaction mixture was stirred at 86° C. (gentle reflux) for 16-24 hours. The reaction mixture was cooled to 75° C. and methanol (1.5 L) was added keeping the internal temperature 50° C.-55° C. The reaction mixture was neutralized (pH 5-7) by adding concentrated HCl (450 mL) over 30 minutes maintaining 60° C.-65° C. The reaction mixture became thicker and lighter in color. Water (3 L) was added to the mixture over 30 minute maintaining 60° C.-65° C. The reaction mixture was cooled to 22° C.-28° C. The product was collected by vacuum filtration followed by waster wash (3×500 mL) and cold (0°-5° C.) methanol (2×300 mL). The product was dried to give the desired product (148 g, 96.5% purity, HPLC). $^1$HNMR (DMSO$_{-d6}$): δ7.75 (d, 2H, J=8 Hz), 7.64 (d,1H, J=2 Hz), 7.30 (m, 5H), 7.17 (brs, 1H), 7.09 (d, 1H, J=2 Hz), 7.07 (s, 1H), 6.81 (dd, 1H, J=9 Hz, 2 Hz), 6.72 (d, 2H, J=9 Hz), 6.55 (d, 1H, J=9 Hz), 4.09 (br m, 2H), 3.16 (br m, 4H), 2.50 (br m, 2H).

EXAMPLE 11

4-{2-[2-(2-Amino-ethyl)-1-benzhydryl-5-chloro-1H-indol-3-yl]-propyl}-benzoic Acid 4-{3-[2-(2-Acetylamino-ethyl)-1-benzhydryl-5-chloro-1H-indol-3-yl]-propyl}-benzoic acid (175 g, 0.310 mol) is added to a stirred solution of methanol (700 mL), water (175 mL) and potassium hydroxide (385 g, 5.83 mol). The mixture is wormed to 86° C. for 16 h-24 h. The reaction is complete when the product/starting material ratio is greater than 99/1 by HPLC. The following addition steps should maintain the reaction mixture at an internal temperature of 60° C.-65° C. Methanol (1500 mL) is added to the reaction mixture. Concentrated HCl (480 mL) is added over a 30 min to the reaction mixture, neutralizing the mixture to a pH of 5 to 7. Precipitation occurs and the reaction mixture becomes lighter. Water (2.5 L) is added over 30 min and stir the reaction mixture for 30 min at 60° C.-65° C. The reaction mixture is cooled to room temperature. The product is collected by filtration and washed with warm water (3×250 mL, 50° C.-60° C.) and cold methanol (250 mL, 0° C.-5° C.). Drying the product in vacuo at 60° C.-70° C. gives 152 g (94%, 95.0% by HPLC) of 4-{2-[2-(2-Amino-ethyl)-1-benzhydryl-5-chloro-1H-indol-3-yl]-propyl}-benzoic acid.

$^1$H NMR (DMSO-$d_6$) δ1.83(br.m, 2H), 2.63(br.m, 4H), 2.72(br.m, 2H), 2.93(br.m, 2H), 6.50(d, 1H), 6.75(d, 1H), 7.08(m, 5H), 7.10(br.s, 1H), 7.33(m, 5H), 7.46(br.s, 1H), 7.75(d, 2H).

EXAMPLE 12

Synthesis of 4-(2-{1-Benzhydryl-5-chloro-2-[2-(3,4-dichlorophenyl-methanesulfonylamino)-ethyl]-1H-indol-3-yl}-ethoxy)-benzoic Acid Bis(trimethylsilyl)trifluoroacetamide (76.4 g, 0.297 mol) was added in one portion to 4-{2-[2-(2-Amino-ethyl)-1-benzhydryl-5-chloro-1H-indol-3-yl]-ethoxy}-benzoic acid (120 g 0.229 mol) suspended in methylene chloride (1 L). The mixture was refluxed for 90 min and allowed to cool to 37 C. pyridine (45.3 g 0.575 mol) was added in one portion followed by dropwise addition of 3,4-dichlorobenzyl-sulfonyl chloride (71.3 g 0.274 mol) in methylene chloride (240 mL). After HPLC analysis showed complete consumption of WAY-195542, the reaction was cooled to 20° C. and acetonitrile (240 mL) was added. The methylene chloride was distilled at 15-25° C. under reduced pressure (35-150 mmHg). Acetonitrile (240 ml) was added and the distillation was continued until methylene chloride was removed. Acetonitrile (1.5 L) was added and the temperature was adjusted to 20° C. A white solid precipitated during the dropwise addition of water (240 ml) over 20 min. The suspension was stirred for another 30 min and the solid was collected by filtration. The cake was washed twice with acetonitrile/water (4:1, 240 ml). The wet material (494 g) was dried in a vacuum oven (70 C, 10 mmHg) over 16 h to obtain the desired product (145 g). The crude compound was suspended toluene (4 mL/g) and the mixture was heated to reflux. The hazy solution was cooled to 45 C over a period of 1 h, seeds were added at 60° C. The suspension was stirred at 45 C for 30 min and the solid was collected by filtration. The cake was washed with toluene. The crude compound was dissolved in ethylacetate (5 mL/g) and filtered. The clear solution was heated to 40 C and heptane (5 mL/g) was added dropwise over a period of 10 min. The mixture was cooled to 20 C and stirred for 16 h. The solid was collected by filtration and the cake was washed with heptane (2 mL/g). The wet cake was dried in a vacuum oven (50 C/10 mmHg) for 16 h to give the desired product (104 g 72%). The structure was determined by $^1$H-NMR. □(300 MHz, DMSO-$d_6$) δ2.98 (m, 2H), 3.04 (m, 2H0, 3.12 (t, J=6.7 Hz, 2H), 4.29 (s, 2H), 6.40 (d, J=8.9 Hz, 1H), 6.74 (dd, J=8.9 Hz, 2.1 Hz, 1H), 6.92 (d, J=8.9 Hz, 1H), 7.02-7.05 (m, 5H), 7.20 (dd, J=8.3 Hz, 1.8 Hz, 1H), 7.29-7.31 m, 6H), 7.47 (d, J=8.3 Hz, 1H), 7.50 (d, J=1.8 Hz, 1H), 7.61 (d, J=2.1 Hz, 1H), 7.80 (d, J=8.9 Hz, 1H) ppm.

EXAMPLE 13

4-(3-{1-Benzhydryl-5-chloro-2-[2-(3,4-dichlorophenylmethanesulfonylamino)-ethyl]-1H-indol-3-yl}-propyl)-benzoic Acid To a suspension of 4-{3-[2-(2-Amino-ethyl)-1-benzhydryl-5-chloro-1H-indol-3-yl]-propyl}-benzoic acid (125.0 g, 0.239 mol) in dichloromethane (1.25 L) at ambient temperature, bis(trimethylsilyl)trifluoroacetamide (89.2 g, 0.347 mol) was added. After refluxing for 0.5 hours, the reaction mixture was cooled to 35° C. To the reaction mixture solution, pyridine (49.1 g, 0.621 mol) and a solution of (3,4-Dichlorophenyl)-methanesulfonyl chloride (68.2 g, 0.263 mol) in dichloromethane (200 mL) were added successively. The reaction mixture was refluxed for 0.5 h and then cooled to room temperature. Water (1.25 L) and conc.HCl (61.6 g) were added to the reaction mixture successively. The organic layer was washed with water (600 mL×2) and concentrated. The concentrate was dissolved in 2-propanol (710 mL) added to cold water (2.45 L) and the crude product (173.0 g, yield 97%, HPLC 78%, SLI 11%) was collected after filtration. Pure 4-(3-{1-Benzhydryl-5-chloro-2-[2-(3,4-dichloro-phenyl-methanesulfonylamino)-ethyl]-1H-indol-3-yl}-propyl)-benzoic acid (WAY-195902, 125.0 g, yield 72%, HPLC 98%, SLI 033%) was obtained by successive treatment of the crude product with a mixture of toluene and heptane followed by a mixture of ethyl acetate and heptane. $^1$H NMR (DMSO$_{-d6}$): δ12.80 (br.s, 1H), 7.89 (d, 2H, J=2 Hz), 7.59 (d, 1H, J=1.5 Hz), 7.53 (d,1H, J=6 Hz), 7.48 (d, 1H, J=1.5 Hz), 7.38 (m, 9H), 7.20 (m, 5H), 6.77 (dd, 1H, J=6.9 & 1.5 Hz), 6.46 (d, 1H, J=6.9 Hz), 4.36 (s, 2H), 3.18 (m,2H), 2.96 (m,2H), 2.76 (m, 4H), 1.90(m, 2H).

Many variations of the present invention not illustrated herein will occur to those skilled in the art. The present invention is not limited to the embodiments illustrated and described herein, but encompasses all the subject matter within the scope of the appended claims.

What is claimed is:

1. A process for preparing a compound of formula (IV):

(IV)

in purified form,
the process comprising converting a compound of formula (III):

(III)

to the compound of formula (IV) by:
using an alkali solution to remove the Y from the ester group in the compound of formula (III), thereby forming a carboxylic acid intermediate;
purifying the carboxylic acid intermediate by slurrying the carboxylic acid intermediate in an organic solvent;
using an alkali solution to hydrolyze the N-acetyl amide bond in the purified carboxylic acid intermediate, thereby forming an amino acid intermediate; and then,
reacting the amino acid intermediate with R-A-$(CH_2)_n$—S(O)$_2$Cl to form the compound of formula (IV);
wherein:
n represents an integer from 0 to 4;
A is a chemical bond, —S—, —O—, —S(O)—, —S(O)$_2$—, —NH—, —C≡C—, R is a moiety selected from the group consisting of $C_1$-$C_6$ alkyl, $C_1$-$C_6$ fluorinated alkyl, $C_3$-$C_6$ cycloalkyl, tetrahydropyranyl, camphoryl, adamantyl, —CN, —N($C_1$-$C_6$ alkyl)$_2$, phenyl, pyridinyl, pyrimidinyl, furyl, thienyl, napthyl, morpholinyl, triazolyl, pyrazolyl, piperidinyl, pyrrolidinyl, imidazolyl, piperizinyl, thiazolidinyl, thiomorpholinyl, tetrazole, indolyl, benzoxazolyl, benzofuranyl, imidazolidine-2-thionyl, 7,7,dimethyl-bicyclo[2.2.1]heptan-2-onyl, benzo[1,2,5]oxadiazolyl, 2-oxa-5-aza-bicyclo[2.2.1]heptanyl, piperazin-2-onyl or pyrrolyl groups, each optionally substituted by from 1 to 3 substituents independently selected from halogen, —CN, —CHO, —CF$_3$, —OCF$_3$, —OH, $C_1$-$C_6$ alkyl, $C_1$-$C_6$ alkoxy, —NH$_2$, —N($C_1$-$C_6$ alkyl)$_2$, —NH($C_1$-$C_6$ alkyl), —NH—C(O)—($C_1$-$C_6$ alkyl), —NO$_2$, —SO$_2$($C_1$-$C_3$ alkyl), —SO$_2$NH$_2$, —SO$_2$NH($C_1$-$C_3$ alkyl), —SO$_2$N($C_1$-$C_3$ alkyl)$_2$, —COOH, —CH$_2$—COOH, —CH$_2$—NH($C_1$-$C_6$ alkyl), —CH$_2$—N($C_1$-$C_6$ alkyl)$_2$, —CH$_2$—NH$_2$, pyridinyl, 2-methyl-thiazolyl, morpholino, 1-chloro-2-methyl-propyl, $C_1$-$C_6$ thioalkyl, phenyl optionally substituted with one or more halogen atoms, benzyloxy, ($C_1$-$C_3$ alkyl)C(O)CH$_3$, ($C_1$-$C_3$ alkyl)OCH$_3$, —C(O)NH$_2$, X represents O or CH$_2$;
Y represents $C_1$-$C_6$ alkyl; and
Z is selected from the group consisting of H, halogen, —CN, —CHO, —CF$_3$, —OCF$_3$, —OH, $C_1$-$C_6$ alkyl, $C_1$-$C_6$ alkoxy, $C_1$-$C_6$ thioalkyl, —NH$_2$, —N($C_1$-$C_6$ alkyl)$_2$, —NH($C_1$-$C_6$ alkyl), —NHC(O)—($C_1$-$C_6$ alkyl), and —NO$_2$; wherein the process is carried out without the use of chromatography.

2. The process of claim 1 wherein n is 1, A is a chemical bond and R is optionally substituted phenyl.

3. The process of claim 2 wherein Z is halo.

4. The process of claim 1, wherein the carboxylic acid intermediate has the formula:

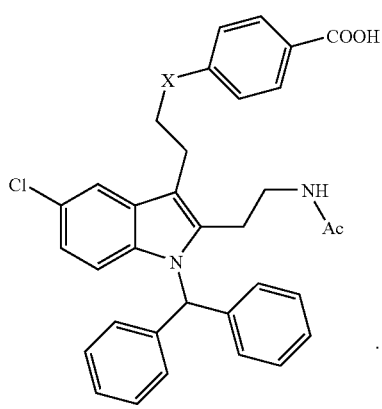

5. The process of claim 1, wherein the organic solvent is selected from the group consisting of ethyl acetate, acetonitrile, a low molecular weight alcohol, and combinations thereof.

6. The process of claim 5, wherein the organic solvent is ethyl acetate.

7. The process of claim 1, wherein the compound of formula (III) is in the form of a crude benzhydrylation product mixture.

8. The process of claim 4, wherein the hydrolysis of the N-acetyl amide bond in the carboxylic acid intermediate is performed using Claisen alkali conditions.

* * * * *

UNITED STATES PATENT AND TRADEMARK OFFICE
CERTIFICATE OF CORRECTION

| | | |
|---|---|---|
| PATENT NO. | : 7,582,771 B2 | Page 1 of 1 |
| APPLICATION NO. | : 10/930534 | |
| DATED | : September 1, 2009 | |
| INVENTOR(S) | : Dehnhardt et al. | |

It is certified that error appears in the above-identified patent and that said Letters Patent is hereby corrected as shown below:

On the cover page,

[*] Notice:   Subject to any disclaimer, the term of this patent is extended or adjusted under 35 U.S.C. 154(b) by 617 days Delete the phrase "by 617 days" and insert -- by 1286 days --

Signed and Sealed this

Twenty-seventh Day of April, 2010

David J. Kappos
*Director of the United States Patent and Trademark Office*